(12) United States Patent
Xu et al.

(10) Patent No.: US 9,982,314 B2
(45) Date of Patent: May 29, 2018

(54) **BACTERIAL STRAIN OF *ACTINOPLANES* SP. AND APPLICATION THEREOF**

(71) Applicant: ZHEJIANG HISUN PHARMACEUTICAL CO., LTD., Zhejiang (CN)

(72) Inventors: Hao Xu, Zhejiang (CN); Fei Tang, Zhejiang (CN); Peijun Zhan, Zhejiang (CN); Jianhong Hu, Zhejiang (CN); Huijun Ren, Zhejiang (CN); Hongmei Fan, Zhejiang (CN); Linghui Zheng, Zhejiang (CN); Hua Bai, Zhejiang (CN)

(73) Assignee: ZHEJIANG HISUN PHARMACEUTICAL CO., LTD., Zhejiang (CN)

( * ) Notice: Subject to any disclaimer, the term of this patent is extended or adjusted under 35 U.S.C. 154(b) by 0 days. days.

(21) Appl. No.: 15/028,577

(22) PCT Filed: Oct. 14, 2014

(86) PCT No.: PCT/CN2014/088536
§ 371 (c)(1),
(2) Date: Apr. 11, 2016

(87) PCT Pub. No.: WO2015/055107
PCT Pub. Date: Apr. 23, 2015

(65) Prior Publication Data
US 2016/0265071 A1    Sep. 15, 2016

(30) Foreign Application Priority Data
Oct. 16, 2013 (CN) .......................... 2013 1 0501389

(51) Int. Cl.
| | |
|---|---|
| *C12N 1/20* | (2006.01) |
| *C12P 21/04* | (2006.01) |
| *C12R 1/045* | (2006.01) |
| *C12P 19/62* | (2006.01) |

(52) U.S. Cl.
CPC ................ *C12R 1/045* (2013.01); *C12N 1/20* (2013.01); *C12P 19/62* (2013.01)

(58) Field of Classification Search
CPC ............ C12R 1/045; C12N 1/20; C12P 19/62
USPC ............................................ 435/252.6, 71.3
See application file for complete search history.

(56) References Cited

U.S. PATENT DOCUMENTS

| | | | |
|---|---|---|---|
| 3,978,211 A | 8/1976 | Coronelli et al. | |
| 4,918,174 A | 4/1990 | McAlpine et al. | |
| 7,378,508 B2 | 5/2008 | Chiu et al. | |
| 7,507,564 B2 | 3/2009 | Shue et al. | |
| 7,863,249 B2 | 1/2011 | Chiu et al. | |
| 8,728,796 B2 | 5/2014 | Shue et al. | |
| 8,859,510 B2 | 10/2014 | Chiu et al. | |
| 8,883,986 B2 | 11/2014 | Chiu et al. | |
| 2006/0257981 A1 | 11/2006 | Shue et al. | |
| 2007/0259949 A1 | 11/2007 | Chiu et al. | |
| 2008/0194497 A1 | 8/2008 | Chiu et al. | |
| 2009/0163428 A1 | 6/2009 | Chiu et al. | |
| 2010/0028970 A1 | 2/2010 | Shue et al. | |
| 2010/0081800 A1 | 4/2010 | Chiu et al. | |
| 2013/0123477 A1 | 5/2013 | Shue et al. | |
| 2013/0252914 A1 | 9/2013 | Chiu et al. | |
| 2013/0266986 A1 | 10/2013 | Malcangi et al. | |
| 2014/0296498 A1 | 10/2014 | Shue et al. | |

FOREIGN PATENT DOCUMENTS

| | | |
|---|---|---|
| CN | 1688707 A | 10/2005 |
| CN | 103275152 A | 9/2013 |
| CN | 103320355 A | 9/2013 |
| CN | 104560766 A | 4/2015 |
| EP | 2647719 A1 | 10/2013 |
| WO | 2008/091554 A1 | 7/2008 |
| WO | 2016/004848 A1 | 1/2016 |

OTHER PUBLICATIONS

International Search Report dated Jan. 12, 2015 issued in corresponding International Patent Application No. PCT/CN2014/088536 (7 pages).
Written Opinion of the International Searching Authority dated Jan. 12, 2015 issued in corresponding International Patent Application No. PCT/CN2014/088536 (5 pages).
Mekonnen Kurabachew et al., "Lipiarmycin targets RNA polymerase and has good activity against multidrug-resistant strains of *Mycobacterium tuberculosis*", Journal of Antimicrobial Chemotherapy. vol. 62. (2008) pp. 713-719.

(Continued)

*Primary Examiner* — Scott Long
*Assistant Examiner* — Paul C Martin
(74) *Attorney, Agent, or Firm* — Millen White Zelano and Branigan, PC; John Sopp

(57) ABSTRACT

A bacterial strain of *Actinoplanes* sp. and and the use thereof. The bacterial strain is named *Actinoplanes* sp. HS-16-20, whose preservation number is CGMCC (China General Microbiological Culture Collection Center) No. 7294. The bacterial strain can be used to generate Fidaxomicin or analogs thereof or compositions containing Fidaxomicin, such as by aerobically fermenting the strain in nutrient medium containing assimilable carbon and/or nitrogen sources. Fidaxomicin has an inhibitory effect on various gram positive bacteria pathogens, and in particular, on *Clostridium difficile*.

9 Claims, 4 Drawing Sheets

(56) References Cited

OTHER PUBLICATIONS

D.G. Pitcher et. al. "Rapid extraction of bacterial genomic DNA with guanidium thiocyanate", Letters in Applied Microbiology, vol. 8. (1989) pp. 151-156.
Yan Xia et al.,"Research of cell compoment and physiological biochemical characteristics of 23 strains from Tibet soil", Journal of Northwest A & F University(Nat. Sci. Ed.). vol. 35, No. 10 Pages (2007) pp. 213-218.
B.Cavalleri et al., "Structure and biological activity of Lipiarmycin B", The Journal of Antibiotics, vol. 3, (1988) pp. 308-315.
International Search Report dated Jan. 12, 2015 issued in corresponding PCT/CN2014/088536 application (pp. 1-2).
English Abstract of CN 103275152 A published Sep. 4, 2013.
English Abstract of CN 103320355 A published Sep. 25, 2013.
Supplementary European Search Report dated May 26, 2017 issued in corresponding EP 14854401 application (8 pages).

BACTERIAL STRAIN OF ACTINOPLANES SP. AND APPLICATION THEREOF

CROSS REFERENCE TO RELATED APPLICATION

The present application is the U.S. national stage application of International Application PCT/CN2014/088536, filed Oct. 14, 2014, which international application was published on Apr. 23, 2015, as International Publication WO2015/055107. The International Application claims priority of Chinese Patent Application 201310501389.3, filed Oct. 16, 2013, the contents of which are incorporated herein by reference in their entireties.

FIELD OF INVENTION

The present invention relates to microorganism engineering technology, in particular to an *Actinoplanes* sp strain and application thereof in preparing Fidaxomicin.

PRIOR ARTS

Diarrhea, colonitis and other intestinal diseases caused by the infection of *clostridium difficile* have features of high pathogenicity and high lethality. In as early as 2003, *clostridium difficile* had given rise to infection epidemic in numerous provinces in Canada. Up to October 2008, a *clostridium difficile* ribosome type 027 with high pathogenicity and high lethality had given rise to nosocomial infection epidemic in at least 40 states in US. Soon after the type 027 was discovered in North America, the fulminant epidemic of *clostridium difficile* appeared in succession in 17 European countries. *Clostridium difficile* has been listed as mandatorily monitored pathogen in Europe. Under the lead of the European Centre for Disease Prevention and Control (ECDC), three epidemiological investigations were conducted in 2002, 2005 and 2008 all over Europe. For a long time, *clostridium difficile*-associated diarrhea (CDAD) has been a major focus of study in the medical field, and it is an important task for pharmaceutical researchers to seek new drugs treating CDAD.

In 2011, FDA authorized Optimer pharmaceutical company to produce a macrolides new drug Fidaxomicin, whose commercial name is Dificid, to treat *clostridium difficile*-associated diarrhea (CDAD). Fidaxomicin is R-Tiacumicin B. In the U.S. Pat. No. 4,918,174 published in 1986, the applicant of which is Robert et al, it was first disclosed that *Dactylosporangium aurantiacum* subsp. *hamdenensis* NRRL 18085 can ferment and produce an antibiotic Tiacumicin and structure thereof to inhibit gram positive bacteria. Lipiarmycins are a group of compouds closely relevant to Tiacumicin. Lipiarmycins A3 and Lipiarmycins B3 are similar to Tiacumicins B and Tiacumicins C (J. Antibiotics, 1988, 308-315), respectively. U.S. Pat. No. 3,978,211 has disclosed that Lipiarmycins and its producer strain *Actinoplanes deccanensis* A/10655 ATCC 21983. The producer strain *Catellatospora* sp. Bp3323-81 of Lipiarmycins A3 was disclosed in J. Antimicrobial Chemotherapy 2008, 62, 713-719. The above producer strains of Tiacumicin and Lipiarmycins have the disadvantages of low potency of target products (Tiacumicin and Lipiarmycins), drastic fluctuation of production, instability and high cost of production. Hence seeking for a new highly-effective producer strain of Fidaxomicin is still on going.

CONTENT OF THE PRESENT INVENTION

One of the aims of the present invention is to provide a new *Actinoplanes* sp HS-16-20, which has the ability to produce Fidaxomicin, with the preservation number of CGMCC No. 7294.

The aim of the present invention is also to provide an *Actinoplanes* sp HS-16-20 (CGMCC No. 7294), which can be used to produce Fidaxomicin and analogue thereof, or can be used to produce pharmaceutical composition containing Fidaxomicin.

The present invention also provides a method of preparing Fidaxomicin and analogue thereof by *Actinoplanes* sp HS-16-20 (CGMCC NO. 7294). The method comprises aerobically fermenting the *Actinoplanes* sp HS-16-20 in nutrient medium containing assimilable carbon and/or nitrogen sources.

Preferably, the assimilable carbon source is selected from the group consisting of saccharose, glucose, fructose, rhamnose, raffinose, xylose, arabinose, industry molasses, lactose, galactose, maltose, mycose, xylan, dextrin, starch, sorbitol, saligenin, inositol, mannitol, glycerol, glycine and inulin.

Preferably, the assimilable nitrogen source is selected from the group consisting of beef extract, salvelike yeast extract, yeast extraction, yeast powder, peptone, tryptone, gluten powder, cottonseed meal, peanut meal, soybean meal, corn steep liquor powder, bran, urea, ammonium salt and nitrate.

Preferably, the temperature of the aerobic fermenting is 20° C. to 40° C., more preferably 25° C. to 30° C.; pH is 6.0-8.0, more preferably 7.0; time is 144-240 hours; aeration rate is 0.5-1.0 vvm.

Preferably, the mode of the aerobic fermenting is submerged fermentation.

The invention also provides a method of separation and purifying Fidaxomicin. The method comprises submitting the fermentation broth to extraction, concentration and column chromatography, etc., to prepare the compound.

Fidaxomicin can be detected by HPLC in the following conditions:

Chromatography Column: C18 Column, 5 μm, 4.6×250 nm;
Mobile phase A: 0.05% phosphoric acid (v/v);
Mobile phase B: 90% acetonitrile (v/v);
Flow rate: 1.00 ml/min;
Detection wavelength: 250 nm;
Program: 0-20 min: 5%-100% phase B; 20-21 min: 100% phase B; 21-22 min: 100%-5% phase B;
Sample volume: 10 μl.

The producer strain of Fidaxomicin of the present invention is *Actinoplanes* sp HS-16-20 (CGMCC NO. 7294).

The *Actinoplanes* sp HS-16-20 (CGMCC NO. 7294) of the present invention was preserved in China General Microbiological Culture Collection Center (Address: NO. 1 West Beichen Road, Chaoyang District, Beijing, Institute of Microbiology Chinese Academy of Sciences) on Mar. 11, 2013, and the preservation number is CGMCC NO. 7294, classification name is *Actinoplanes* sp. The *Actinoplanes* sp HS-16-20 (CGMCC NO. 7294) has been registered and proved viable.

The main biological features of *Actinoplanes sp* HS-16-20 of the invention are: The color of the colony is croci, and the colonial morphology is round, with a ruga and embossmen on the surface. The diameter of the colony is middle sized, about 6 mm. The colony is humidish, and the hyphae are loosely in touch with the medium and can be picked easily.

The present invention describes the feature in morphological and molecular level of *Actinoplanes* sp HS-16-20. Compared with the features of known producer strains of Tiacumicin and Lipiarmycins in morphology and molecular level, it can be ascertained that *Actinoplanes* sp HS-16-20 belongs to *Actinoplanes* sp, however, as a brand-new strain, it is different from the known producer strains of Tiacumicin and Lipiarmycins, *Dactylosporangium aurantiacum* subsp. *hamdenensis* NRRL 18085, *Actinoplanes deccanensis* A/10655 ATCC 21983 and *Catellatospora* sp. Bp3323-81.

The *Actinoplanes* sp HS-16-20 of the present invention has following advantages compared to the producer strains of Fidaxomicin in prior arts:

The *Actinoplanes* sp HS-16-20 of the present invention enhances the fermentation unit. The *Actinoplanes* sp HS-16-20 of the invention produces substantially larger amount of Fidaxomicin and analogue thereof compared to the original strains and is beneficial for industrial production.

DETAILED DESCRIPTION OF THE PREFERRED EMBODIMENT

Figure 1:
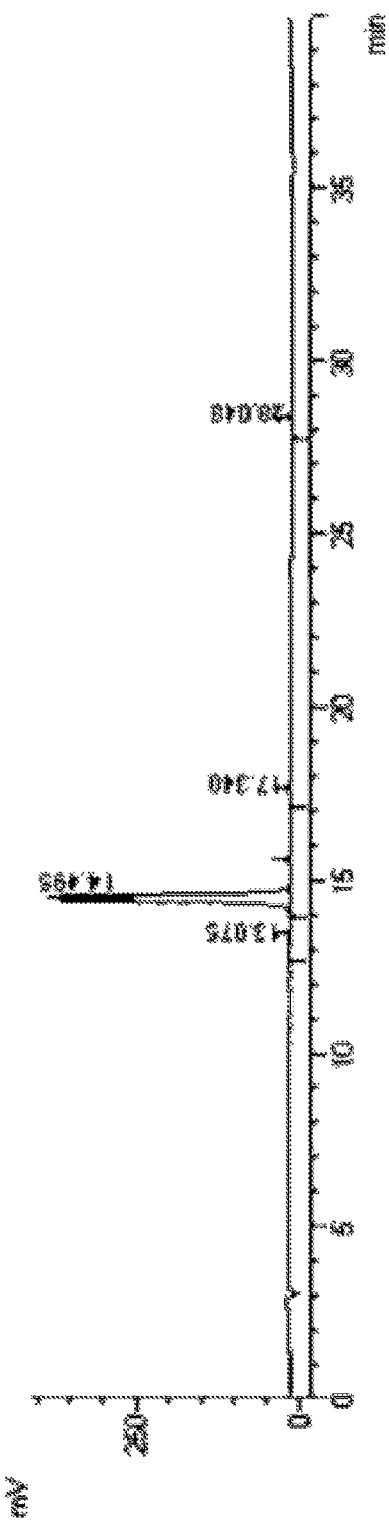
FIG. 1 is a HPLC figure of pure Fidaxomicin obtained in Example 8 of the invention.
Figure 2:
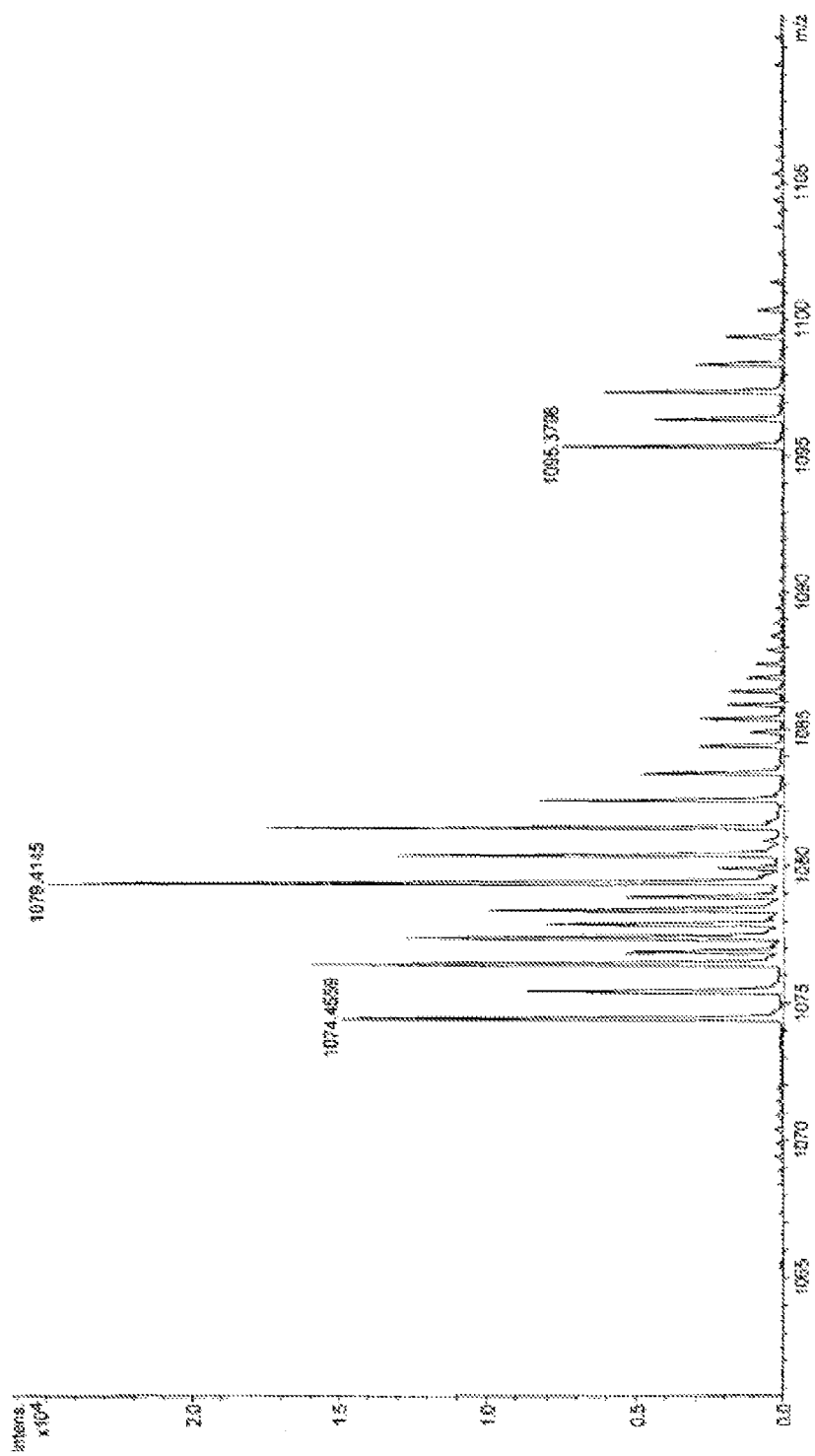
FIG. 2 is a ESI/MS figure of pure Fidaxomicin obtained in Example 8 of the invention.
Figure 3:
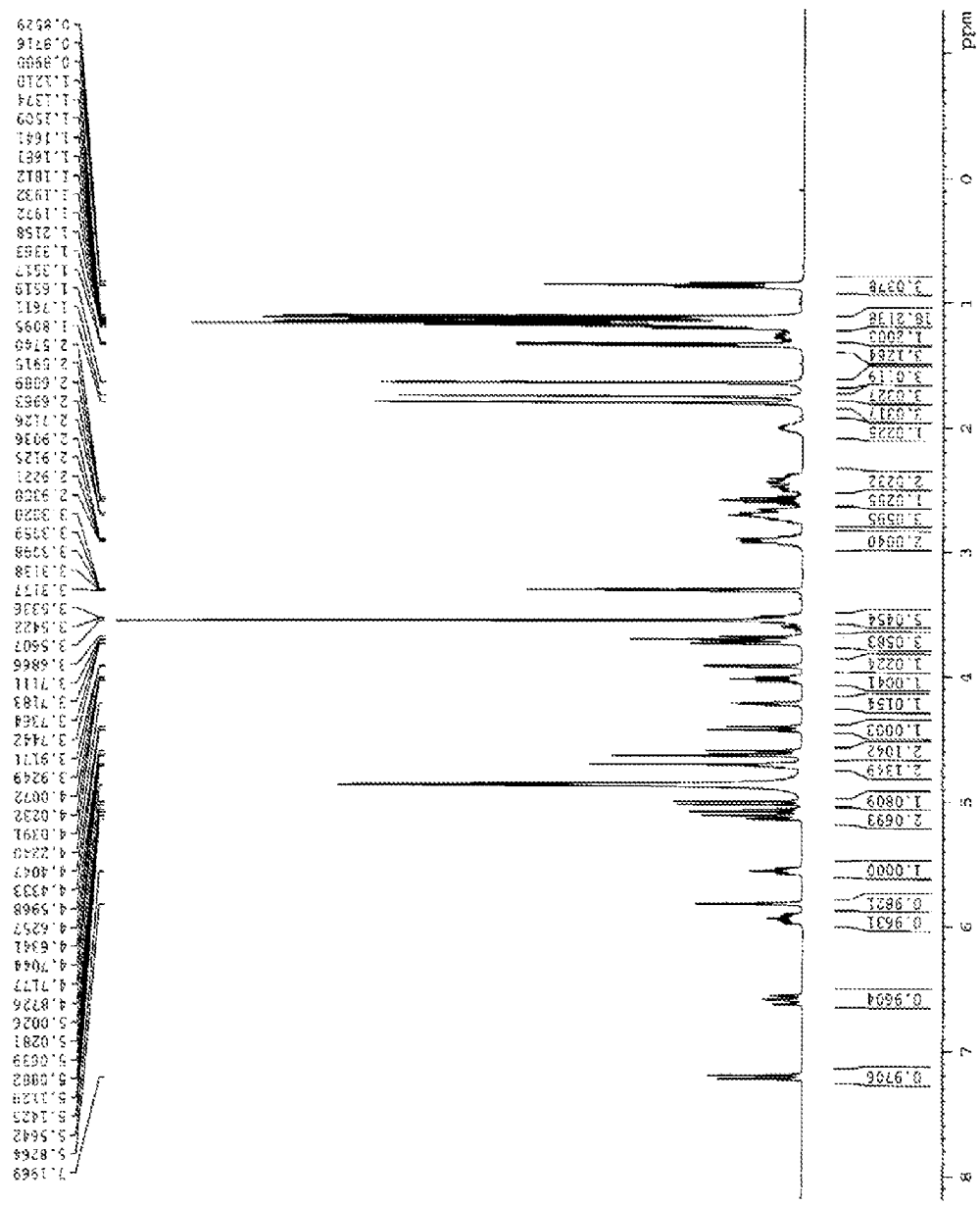
FIG. 3 is a $^1$H-NMR figure of pure Fidaxomicin obtained in Example 8 of the invention.
Figure 4:
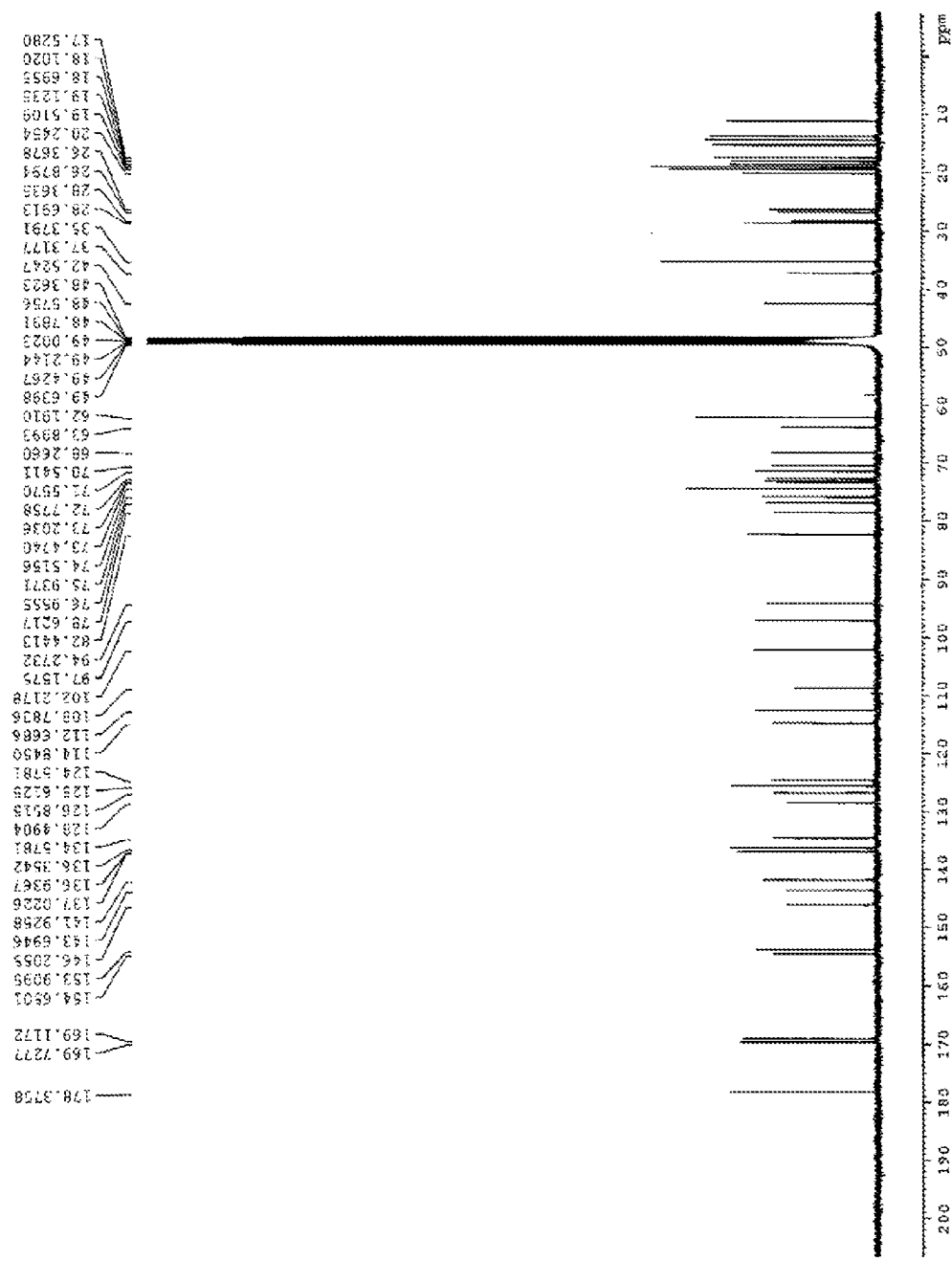
FIG. 4 is a $^{13}$C-NMR figure of pure Fidaxomicin obtained in Example 8 of the invention.

The reagent used to adjust the pH of liquid culture medium of the following examples is NaOH solution or hydrochloric acid regularly used in the art.

Water is used to obtain a needed volume of various culture media in the following examples. Weigh the materials according to the recipe and mix the materials thoroughly, then add water to the needed volume, and lastly use NaOH solution or hydrochloric to adjust pH as needed.

The formula of used media of the invention are as follows:

ISP1 medium (g/L): glycerinum 10.0, asparagine 1.0, $K_2HPO_4$ 1.0, trace element solution 1.0 ml, agar 15.0, pH7.0-7.4. The components of the trace element solution are (g/L): $FeSO_4.7H_2O$ 0.1, $MnCl_2.4H_2O$ 0.1, $ZnSO_4.7H_2O$ 0.1.

ISP2 medium (g/L): yeast extract powder 4.0, malt extract powder 10.0, glucose 4.0, agar 15.0, pH 7.3.

ISP3 medium (g/L): oat agar 72.5, agar 2.5, trace element solution 1.0 ml, pH 7.0-7.4. The components of the trace element solution are (g/L): $FeSO_4.7H_2O$ 0.1, $MnCl_2.4H_2O$ 0.1, $ZnSO_4.7H_2O$ 0.1.

ISP4 medium (g/L): soluble starch 10.0, $K_2HPO_4$ 1.0, $MgSO_4.7H_2O$ 1.0, NaCl 1.0, $(NH_4)_2SO_4$ 2.0, $CaCO_3$ 2.0, trace element solution 1.0 ml, agar 15.0, pH 7.0-7.4. The components of the trace element solution are (g/L): $FeSO_4.7H_2O$ 0.1, $MnCl_2.4H_2O$ 0.1, $ZnSO_4.7H_2O$ 0.1.

ISP5 medium (g/L): glucose 10.0, asparagine 0.5, $K_2HPO_4$ 0.5, agar 15.0, pH 7.0-7.4.

ISP9 medium (g/L): $(NH_4)_2SO_4$ 2.64, $KH_2PO_4$ 2.38, $K_2HPO_4$ 5.65, $MgSO_4.7H_2O$ 1.00, $CaCl_2.2H_2O$ 0.10, agar 15.00, trace element solution 1 ml. The components of the trace element solution are (g/L): $CuSO_4.5H_2O$ 0.64, $FeSO_4.7H_2O$ 0.11, $MnCl_2.4H_2O$ 0.79, $ZnSO_4.7H_2O$ 0.15.

Gauserime 1 synthetic agar medium (g/L): soluble starch 20.0, $KNO_3$ 1.0, $K_2HPO_4$ 0.5, $MgSO_4.7H_2O$ 0.5, NaCl 0.5, $FeSO_4.7H_2O$ 0.01, pH 7.2-7.4.

Calcium malate agar medium (g/L): calcium malate 10.0, glycerinum 10.0, $K_2HPO_4$ 0.05, $NH_4Cl$ 0.5, agar 15.0, pH 7.2-7.4.

LB medium (g/L): tryptone 10.0, NaCl 10.0, yeast extract 5.0, agar 15.0, pH 7.0.

YMS medium (g/L): yeast extract 4.0, malt extract 10.0, glucose 4.0, micro liquid 5 ml. The components of the micro liquid are (g/L): $MgSO_4.7H_2O$ 80.0, $CaCO_3$ 20.0, $FeSO_4.7H_2O$ 6.0 $ZnSO_4.7H_2O$ 2.0, $MnSO_4.7H_2O$ 2.0, $CoCl_3.6H_2O$ 0.5, $NaMoO_4.2H_2O$ 1.0.

Czapek Dox Agar medium (g/L): saccharose 30.0, $NaNO_3$ 3.0, $K_2HPO_4$ 1.0, $MgSO_4.7H_2O$ 0.5, KCl 0.5, $FeSO_4.7H_2O$ 0.01, agar 20.0, pH 6.0-6.5.

GYEA medium (g/L): glucose 10.0, yeast extract powder 10.0, pH6.8.

The sources of the strains used for comparison in the present invention are as follows:

*Dactylosporangium aurantiacum* subsp. *hamdenensis* NRRL 18085 is purchased from NRRL (Agricultural Research Service Culture Collection).

*Actinoplanes deccanensis* A/10655 ATCC 21983 is purchased from ATCC (American type culture collection).

*Catellatospora* sp. Bp3323-81 is purchased from Novartis, Switzerland.

Example 1: Source of the Strain

*Actinoplanes* sp. HS-16-20 CGMCC NO. 7294 is an actinomycetes strain isolated from a soil sample on the top of Mount Baiyun, Taizhou, Zhejiang.

Cross-sampling in the delimited region in Baiyun, Taizhou was performed, and five sampling sites were picked at random. 10 g of soil sample was collected at each site and put into a conical flask. 10 g of the sample was picked out after being well-mixed, and was added into a conical flask containing 90 mL deionized water with a magnetic stirring apparatus inside, and vortexed for 30 mins to allow the sample to blend into turbid liquid, and that was $10^{-1}$ bacterial liquid. The bacterial liquid was diluted by 1:9 using aquae sterilisata to reach the concentrations of $10^{-2}$, $10^{-3}$, $10^{-4}$ and $10^{-5}$ respectively according to the spread plate method. 0.1 mL of the bacterial liquid of different dilution ratio was spread on ISP2 medium-coated plates by slight spreading on the surface of the culture medium using a sterilized spreader. The plate stood for 30 min at room temperature and then was placed in an incubator set at 28° C. When the colonies appeared, the colour, transparency, surface and morphology of the rim of the colonies were observed in order to check that the characteristics are consistent. The colonies with consistent morphological characteristics were picked and seeded, and the seeded plate was placed in an incubator set at 28° C. and cultured for 8 days. 1000 preliminarily screened strains were picked upon maturation of the hyphae, and were scraped using inoculating shovel under aseptic condition, and then were inoculated into 250 mL conical flasks (containing 25 mL seed medium each) and cultured by shaking at 28° C. for 28 hours to obtain the seed solution. The seed solution was inoculated into 250 mL conical flasks (containing 20 mL of fermentation medium each), respectively with an transfer amount of 15-20% of the seed solution and cultured by shaking at 28° C. for 8 days. The content of Fidaxomicin obtained from the fermentation broth was detected by HPLC, and the strain *Actinoplanes* sp. HS-16-20 was selected as the most productive strain.

Example 2: The Morphological and Culture Characteristics of *Actinoplanes* sp. HS-16-20, CGMCC NO. 7294

Experiments were conducted according to Manual of Systematic Identification of Common Bacteria, Molecular Cloning: A Laboratory Manual and Chinese Pharmacopoeia (2010 Edition). The experiments regarding morphological and culture characteristics were performed using 10 media, namely ISP1, ISP2, ISP3, ISP4, ISP5, Gauserime 1 synthetic agar medium, calcium malate agar medium, LB, YMS and Czapek Dox Agar medium. After being cultured at 28° C. for 7-10 days, the colour and pigment of the mycelia were observed, and the results are shown in Table 1.

TABLE 1

Culture Characteristics of *Actinoplanes* sp. HS-16-20 in 10 media

| Medium | Growth Situation | Substrate mycelium | Aerial mycelium | Soluble pigment |
|---|---|---|---|---|
| ISP1 | 2 | Deep yellow | Deep yellow | NO |
| ISP2 | 4 | Sunny yellow | creamy yellow | NO |
| ISP3 | 3 | creamy yellow | creamy yellow | NO |
| ISP4 | 3 | beige | beige | NO |
| ISP5 | 3 | Light ivory | Light ivory | NO |
| Gauserime 1 | 2 | Light ivory | Light ivory | NO |
| calcium malate | 2 | Light ivory | Light ivory | NO |
| LB | 3 | beige | beige | NO |
| YMS | 3 | Deep yellow | Deep yellow | NO |
| Czapek Dox | 2 | Light gray close to white | Light gray close to white | NO |

Example 3: The Physiological and Biochemical Characteristics of *Actinoplanes* sp. HS-16-20, CGMCC NO. 7294

Utilization of carbon source: ISP9 medium was used as basal medium with the final concentration of each carbon source being 1.0%. The results are shown in Table 2.

Utilization of nitrogen source: ISP9 medium was used as basal medium with the final concentration of both potassium nitrate and ammonium sulfate being 0.1%. And the results are shown in Table 2.

The basal medium used in the degradation assay and NaCl tolerance assay is GYEA (pH 6.8). The results of degradation assay are shown in Table 3. The results of the NaCl tolerance assay is that *Actinoplanes sp*. HS-16-20 tolerates NaCl well and can still survive under the concentration of 10%.

The medium used in oxidase assay, catalase assay, pH assay and temperature assay is YMS medium. The result is that strain can grow between 14° C.–45° C., the optimum growth temperature is 28° C.; The strain can grow at pH 5.0-7.5, and the optimum range is pH 6.5-7.0. The results of the oxidase and catalase assay are shown in Table 4.

The M.R, V-P and urease assay were performed according to the method of Manual of Systematic Identification of Common Bacteria. And the results are shown in Table 4.

The physiological and biochemical assay: cultured for 7-9 days at 28° C. except for the temperature assay. And the results are shown in Table 4.

TABLE 2

Utilization of carbon source and nitrogen source of *Actinoplanes* sp. HS-16-20

| Carbon source | Growth Situation | Carbon source | Growth Situation | Inorganic nitrogen | Growth Situation |
|---|---|---|---|---|---|
| D-glucose | 3 | saligenin | 3 | ammonium sulfate | + |
| D-raffinose | 1 | D-lactose | 3 | potassium nitrate | + |
| D-xylose | 1 | galactose | 3 | | |
| D-sorbitol | 2 | inositol | 2 | | |
| L-arabinose | 1 | mannitol | 2 | | |
| glycerinum | 2 | glycine | 1 | | |
| maltose | 3 | xylan | 3 | | |
| D-fructose | 2 | inulin | 2 | | |
| D-saccharose | 2 | rhamnose | 2 | | |

TABLE 3

The results of degradation assay of *Actinoplanes* sp. HS-16-20

| Degradation product | Concentration of degradation product | Result | Degradation product | Concentration of degradation product | Result |
|---|---|---|---|---|---|
| adenine | 0.5% | 0 | casein | 1.0% | 1, − |
| guanine | 0.5% | 4, − | tyrosine | 1.0% | 4, − |
| xanthine | 0.4% | 4, − | Tween-40 | 1.0% | 3, − |
| hypoxanthine | 0.4% | 4, − | Tween-60 | 1.0% | 3, − |
| xylan | 0.4% | 4, + | Tween-80 | 1.0% | 3, + |

TABLE 4

The main physiological and biochemical characteristics of *Actinoplanes* sp. HS-16-20

| Test item | Result | Test item | Result | Test item | Result |
|---|---|---|---|---|---|
| gelatin liquefaction | − | Production of hydrogen sulfide | − | catalase | − |
| amylohydrolysis | + | V-P test | − | oxidase | − |
| Milk-clotting | − | M.R test | − | Urease test | + |
| Milk peptonization | − | nitrate reduction | + | | |

Note:
in the Table 1-4,
0: no growth;
1: weak growth;
2: can grow;
3: grow well;
4: grow best;
+: Positive;
−: Negative.

Example 4: Sequence Analysis of 16S rNA and the Identification of the Strain

The fresh bacterial bodies of the strain to be tested were collected and total DNA template was extracted according to the Pitcher method that was upgraded from the lysozyme method (Letters in Applied Microbiology, 1989, 8:151-156). Universal primers 27F and 1495R were used to amplify 16S rRNA gene. The PCR product was directly submitted to sequencing by Sangon Biotech (Shanghai) Co., Ltd. after detection and purification. The sequenced 16S rDNA sequence was aligned with the homologous sequences of related species and genus in GENBANK® using BLAST to confirm the taxonomic status of the strain.

The results of BLAST comparison between strain *Actinoplanes* sp. HS-16-20 (CGMCC NO. 7294) 16S rDNA and related sequences in GENBANK® are shown in Table 5 (only strains of great homology are shown in the table).

TABLE 5

The homology of strain HS-16-20 and related strains

| Species | GENBANK ® No. | Number of base differences | Homology (%) |
|---|---|---|---|
| *Actinoplanes deccanensis* | AB036998.1 | 3 | 99.8 |
| *Actinoplanes deccanensis* subsp. *salmoneus* | AB675009.1 | 14 | 99.0 |
| *Actinoplanes* sp. Y16 | HQ839788.1 | 18 | 98.7 |
| *Actinoplanes deccanensis* strain 1MSNU 20026 | NR 042012.1 | 23 | 98.4 |

Through sequencing of the 16S rDNA region, it was found that the strain HS-16-20 (CGMCC NO. 7294) share great homology with *Actinoplanes* sp, the greatest being 99%. Meanwhile the assay for the apparent characteristics of the strain HS-16-20 (CGMCC NO. 7294) was conducted, which revealed that the classification-related parameters of the strain are very close to those of *Actinoplanes* sp, so the strain HS-16-20 (CGMCC NO. 7294) was identified as a strain of *Actinoplanes* sp.

Comparisons between strain *Actinoplanes* sp. HS-16-20 (CGMCC NO. 7294) and other producer strains of Tiacumicin and Lipiarmycins.

According to the report of U.S. Pat. No. 4,918,174, the producer strain of Tiacumicin, *Dactylosporangium aurantiacum* subsp. *hamdenensis* NRRL 18085 can grow in calcium malate agar medium, while grow poorly in Czapek Dox Agar medium. The colour of the substrate mycelium is saffron yellow and the there is no aerial mycelium. Physiological and biochemical characteristics thereof are: gelatin liquefaction negative (−), amylohydrolysis positive (+), milk-clotting negative (−), milk peptonization positive (+), production of hydrogen sulfide positive (+), nitrate reduction positive (+); while *Actinoplanes* sp. HS-16-20 can grow in Czapek Dox Agar medium, and has aerial mycelium with milk peptonization negative (−), production of hydrogen sulfide negative (−).

It is reported in U.S. Pat. No. 3,978,211 that the producer strain of Lipiarmycins *Actinoplanes deccanensis* A/10655 ATCC 21983 grow poorly in both calcium malate agar medium and Czapek Dox Agar medium. The colours of the colony in different media vary from light yellow to saffron yellow, and there is no aerial mycelium. Physiological and biochemical characteristics thereof are: gelatin liquefaction positive (+), amylohydrolysis positive (+), milk-clotting negative (−), milk peptonization negative (−), production of hydrogen sulfide negative (−), nitrate reduction positive (+); while *Actinoplanes* sp. HS-16-20 can grow in calcium malate agar medium and Czapek Dox Agar medium, and has aerial mycelium in different media with gelatin liquefaction negative (−).

*Antimicrobial Chemotherapy* 2008, 62, 713-719 and Journal of Northwest A&F University (Natural Science Edition) 2007, 35(10), 213-218 report that the producer strain of Lipiarmycins *Catellatospora* sp can grow in Gauserime 1 synthetic agar medium, and there is no report regarding its growth situation in other media. Substrate mycelia thereof are not fractured, and single or clustered short chain of spores appear on the agar surface, and there is no aerial mycelium. Physiological and biochemical characteristics thereof are: amylohydrolysis positive (+), milk-clotting negative (−), milk peptonization positive (+), production of hydrogen sulfide negative (−); while *Actinoplanes* sp. HS-16-20 has aerial mycelium in Gauserime 1 synthetic agar medium with milk peptonization negative (−).

Combining the morphological, culture, physiological and biochemical characteristics and the identification results of DNA sequence of *Actinoplanes* sp. HS-16-20 (CGMCC NO. 7294) of the invention, it is known that the strain *Actinoplanes* sp. HS-16-20 (CGMCC NO. 7294) belongs to actinomyces, and is different from any known producer strains of Tiacumicin and Lipiarmycins. So *Actinoplanes* sp. HS-16-20 (CGMCC NO. 7294) is a brand-new bacteria species.

Example 5: Production of Fidaxomicin (1) Preparation and Culture of Colonies on the Plate The plate coated with ISP2 medium (g/L): glucose 4.0, yeast extract 4.0, malt extract 10.0, agar 15.0, distilled water 1000 mL, pH 7.3. Pressure of autoclaving was 1.05 kg/cm$^2$, 20 min. The medium was cooled to 50-60° C. before being poured into the plates. And one loop of bacterial bodies was inoculated and cultured at 28±1° C. for 8 days until the hypha was mature.

(2) Preparation and Culture of Seed Solution

The formula of seed medium (g/L): saccharose 2, sorbitol 3, cottonseed meal 3, peanut meal 1.5, CaCO$_3$ 0.6, MgSO$_4$.7H$_2$O 0.3, pH 7.2. The liquid volume of the shake flask was 25 mL/250 mL, and the autoclaving was performed at 121° C. for 30 minutes. The inoculation amount of the bacteria bodies was 10$^5$-10$^6$ c.f.u./mL, and was cultured at 28±1° C., 250 rpm, for 28 hours by shaking on a shaker. At this point the pH of the culture solution is 6.8-7.0, and the concentration of the hypha was 25-30% (v/v).

(3) Preparation and Culture of Fermentation Broth

The formula of fermentation broth (g/L): saccharose 10, sorbitol 2, soluble starch 3, (NH$_4$)$_2$SO$_4$ 0.5, beef extract 2, peasant meal 1, KH$_2$O$_4$ 0.04, pH 7.0. The liquid volume of the shake flask was 20 mL/250 mL, and the autoclaving was performed at 121° C. for 20 minutes. The inoculation amount of the seed solution was 15-20% (v/v), and was cultured at 28±1° C., 250 rpm, for 8 days by shaking on a shaker. HPLC was conducted after fermentation. The fermentation unit was 5250 μg/mL.

Example 6: Production of Fidaxomicin

As for the preparation of the colonies on the plate and the seed solution please refer to Example 5.

The formula of fermentation broth (g/L): maltodextrin 6, soluble starch 8, lactose 2, soybean meal 1.5, gluten powder 1, yeast powder 1, CaCO$_3$ 0.4, KCl 0.2, MgCl$_2$.7H$_2$O 0.2, pH 7.0. The liquid volume of the shake flask was 25 mL/250 mL, and the autoclaving was performed at 121° C. for 20 minutes. The inoculation amount of the seed solution was 20% (v/v), and was cultured at 30±1° C., 250 rpm, for 8 days by shaking on a shaker. HPLC was conducted after fermentation, and the fermentation unit was 3892 μg/mL.

Example 7: Production of Fidaxomicin

As for the preparation of the colonies on the plate and the seed solution please refer to Example 5.

The formula of fermentation broth (g/L): industrial trial molasses 8, fructose 2, glycerol 3, maltose 3, peptone 1, tryptone 1.5, salvelike yeast extract 0.5, beef extract 0.5, urea 0.2, citric acid triamine 0.5, $MgSO_4 \cdot 7H_2O$ 0.2, $CaCl_2$ 0.4, pH 7.0. The liquid volume of the shake flask was 40 mL/500 mL, and the autoclaving was performed at 121° C. for 20 minutes. The inoculation amount of the seed solution was 10% (v/v), and was cultured at 30±1° C., 250 rpm, for 9 days by shaking on a shaker. HPLC was conducted after fermentation. The fermentation unit was 3156 μg/mL.

Example 8: Preparation and Separation and Purification of Fidaxomicin (1) Preparation Seed Solution in Seeding Tank 10 L of seed medium was added into a 15 L seeding tank (the formula of the seed medium was the same as that in example 5) and sterilized at 121° C. for 30 minutes. After cooling, 100 mL of shake flask seed solution was added, and was cultured at 28±1° C. with a stirring speed of 200 rpm for 24 hours with an aeration rate of 1.0 vvm. At that time the pH of the culture solution was 6.8-7.0, and the concentration of hypha was 25-30% (v/v).

(2) Preparation of Fermentation Tank Medium and Culture

The formula of the fermentation medium was the same as that in example 5, however, 1% PPG was added as defoamer.

The volume of the fermentation tank was 50 L and the volume of the material amount was 35 L, pH 7.0, then it was sterilized at 121° C. for 20 minutes. After cooling, 3.5 L of the seed tank culture solution was added. The fermentation temperature was 28±1° C., and the stirring speed was 200-300 rpm. The fermentation lasted for 8 days with an aeration rate of 0.8-1.0 vvm. Then the fermentation tank was opened, and the concentration of hypha was tested to be 4855 μg/mL.

(3) Extraction of the Fermentation Solution

30 L of the fermentation solution of the above opened fermentation tank was frame filtered, and the filter cake was soaked with 30 L absolute ethyl alcohol, evenly stirred and stood at room temperature for 30 minutes. The organic phase of the supernatant was collected, mixed and stored.

(4) Concentration of the Organic Phase and Resin Column Chromatography

The above mixed organic phase was vacuum concentrated at −0.1 Mpa to 15 L at 40° C. water bath. The concentrated solution was adsorbed by 4 L macroreticular resin HZ20, and eluted by absolute ethyl alcohol. The eluate was collected and vacuum concentrated until dried. Then 72.8 g crude product was obtained.

(5) Purification of the Crude Product and the Structure Identification of the Pure Product All the above crude product was dissolved in methyl alcohol and was applied to a preparative column (120 g 100-200 mesh C18 reversed-phase preparation material was added into the preparative column). 50% (v/v) acetonitrile was used as eluent. Fractions were collected fractionally. The fractions with chromatographic purity greater than 99% and various impurities less than 0.1% were selected to be the major fraction. The major fraction was dried to get 29.1 g pure product and purity thereof was 99.7%. The obtained pure product was analyzed by HPLC, and the spectrogram of HPLC was shown in FIG. 1. The parameters of HPLC were: chromatography column: C18 Column, 5 μm, 4.6×250 nm; mobile phase A: 0.05% phosphoric acid (v/v); mobile phase B: 90% acetonitrile (v/v); flow rate: 1.00 ml/min; detection wavelength: 250 nm; program: 0-20 min: 5%-100% B phase; 20-21 min: 100% B phase; 21-22 min: 100%-5% B phase; Sample volume: 10 μL. After MS analysis of the obtained pure product, the molecular weight thereof was identified as 1058.04.

And through $^1$H-NMR and $^{13}$C-NMR analysis, it was confirmed that the pure product was Fidaxomicin with the structure as follows:

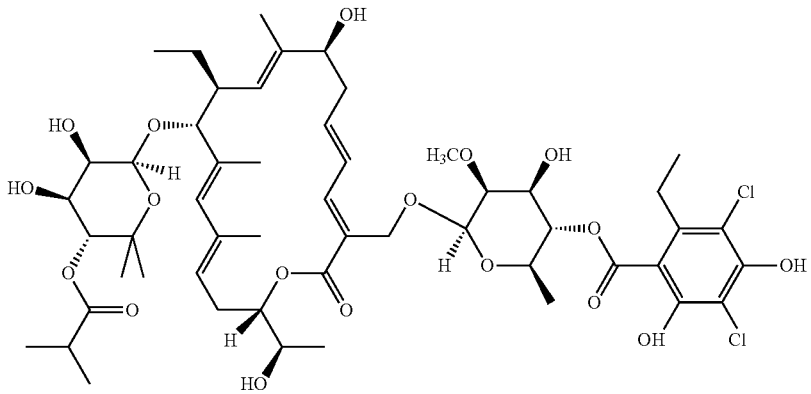 [SMILES: CCc1c(Cl)c(O)c(Cl)c(O)c1C(=O)O[C@H]1[C@H](O)[C@H](OC)[C@H](OC/C2=C\C=C\C[C@H](O)/C(C)=C/[C@H](CC)[C@@H](O[C@H]3OC(C)(C)[C@H](OC(=O)C(C)C)[C@@H](O)[C@H]3O)/C(C)=C/C(C)=C/C[C@@H]([C@@H](C)O)OC2=O)O[C@@H]1C]

Example 9 Comparison of the Capacity of Fidaxomicin Production of Different Bacterial Species The formula of the medium and culture conditions in example 5 were used to culture *Actinoplanes* sp. HS-16-20 (CGMCC NO. 7294) of the invention and other producer strains of Fidaxomicin, respectively. The potency was tested respectively, and the results were shown in the table 6.

TABLE 6

Table of comparison of the capacity of Fidaxomicin production of different bacterial species

| species | potency (μg/mL) |
|---|---|
| *Dactylosporangium aurantiacum* subsp. *hamdenensis* NRRL 18085 | <100 |
| *Actinoplanes deccanensis* A/10655 ATCC 21983 | 200-300 |
| *Catellatospora* sp. Bp3323-81 | <100 |
| *Actinoplanes* sp. HS-16-20(CGMCC NO. 7294) | 3000-6000 |

Combining the morphological, culture, physiological and biochemical characteristics and identification results of DNA sequence of the above four bacterial species, the difference of the production capacity may be caused by different traits of the bacterial species. Inversely the difference of the production capacity can prove indirectly that *Actinoplanes* sp. HS-16-20 (CGMCC NO. 7294) of the invention is a brand-new bacterial species.

Summarizing the above bacterial species, *Actinoplanes* sp. HS-16-20 (CGMCC NO. 7294) of the invention has greatly enhanced the capacity of Fidaxomicin production compared with other strains, which means is beneficial for industrial production.

The embodiments illustrated and discussed in this specification are intended only to teach those skilled in the art the best way known to the inventors to make and use the invention. Modifications and variation of the above-described embodiments of the invention are possible without departing from the invention, as appreciated by those skilled in the art in light of the above teachings. It is therefore understood that, within the scope of the claims and their equivalents, the invention may be practiced otherwise than as specifically described.

What is claimed is:

1. A composition comprising: a bacterial strain of *Actinoplanes* sp HS-16-20, wherein the preservation number is CGMCC No. 7294; and a nutrient medium containing an assimilable nitrogen source selected from the group consisting of: beef extract, yeast extract, yeast powder, peptone, tryptone, gluten powder, cottonseed meal, peanut meal, soybean meal, corn steep liquor powder and bran: wherein the composition is capable of producing Fidaxomicin upon fermentation.

2. The composition of claim 1, wherein the composition comprises an assimilable carbon source which is selected from the group consisting of saccharose, glucose, fructose, rhamnose, raffinose, xylose, arabinose, industrial molasses, lactose, galactose, maltose, mycose, xylan, dextrin, starch, sorbitol, saligenin, inositol, mannitol, glycerol, glycine and inulin.

3. A method for the preparation of Fidaxomicin, comprising, aerobic fermenting of a composition comprising: a bacterial strain of *Actinoplanes* sp HS-16-20, wherein the preservation number is CGMCC No. 7294; and a nutrient medium containing an assimilable carbon source and/or nitrogen source; wherein the composition is capable of producing Fidaxomicin upon fermentation.

4. A method according to claim 3, wherein the composition comprises an assimilable carbon source which is selected from the group consisting of saccharose, glucose, fructose, rhamnose, raffinose, xylose, arabinose, industrial molasses, lactose, galactose, maltose, mycose, xylan, dextrin, starch, sorbitol, saligenin, inositol, mannitol, glycerol, glycine and inulin.

5. A method according to claim 3, wherein the composition comprises as assimilable nitrogen source which is selected from the group consisting of: beef extract, yeast extract, yeast powder, peptone, tryptone, gluten powder, cottonseed meal, peanut meal, soybean meal, corn steep liquor powder, bran, urea, ammonium salt and nitrate.

6. A method according to claim 3, wherein the temperature of the aerobic fermenting is 20° C. to 40° C., pH is 6.0-8.0, time is 144-240 hours.

7. A method according to claim 6, wherein the temperature of the aerobic fermenting is 25° C. to 30° C., pH is 7.0.

8. A method according to claim 3, wherein the aerobic fermenting is conducted with an aeration rate of 0.5-1.0 vvm.

9. A method according to claim 3, wherein the mode of the aerobic fermenting is submerged fermentation.

* * * * *